United States Patent
Porter et al.

(10) Patent No.: US 9,072,647 B2
(45) Date of Patent: Jul. 7, 2015

(54) MODULAR SUPPORT SYSTEM

(71) Applicants: Ryan J. Porter, Kingman, AZ (US); Brett N. Chapman, Kingman, AZ (US); Matthew A. Del Bianco, Whitman, AZ (US); Robert Q. Riley, Phoenix, AZ (US); Ronald A. Dicarlo, Kingman, AZ (US)

(72) Inventors: Ryan J. Porter, Kingman, AZ (US); Brett N. Chapman, Kingman, AZ (US); Matthew A. Del Bianco, Whitman, AZ (US); Robert Q. Riley, Phoenix, AZ (US); Ronald A. Dicarlo, Kingman, AZ (US)

( * ) Notice: Subject to any disclaimer, the term of this patent is extended or adjusted under 35 U.S.C. 154(b) by 181 days.

(21) Appl. No.: 13/986,199

(22) Filed: Apr. 11, 2013

(65) Prior Publication Data

US 2013/0269711 A1    Oct. 17, 2013

Related U.S. Application Data

(60) Provisional application No. 61/686,866, filed on Apr. 13, 2012.

(51) Int. Cl.
| | |
|---|---|
| *A61F 5/37* | (2006.01) |
| *A61G 99/00* | (2006.01) |
| *A61G 1/013* | (2006.01) |
| *A61G 1/044* | (2006.01) |
| *A61G 1/048* | (2006.01) |
| *A61G 13/12* | (2006.01) |

(52) U.S. Cl.
CPC ............... *A61G 99/00* (2013.01); *A61G 1/013* (2013.01); *A61G 1/044* (2013.01); *A61G 1/048* (2013.01); *A61G 13/121* (2013.01); *A61F 5/3776* (2013.01); *A61G 2200/325* (2013.01); *A61G 2200/327* (2013.01)

(58) Field of Classification Search
CPC .... A61F 5/3776; A61G 13/121; A61G 1/013; A61G 1/044; A61G 1/048; A61G 2200/325; A61G 2200/327; A61G 99/00
See application file for complete search history.

(56) References Cited

U.S. PATENT DOCUMENTS

| | | | | |
|---|---|---|---|---|
| 3,133,295 | A * | 5/1964 | Klingensmith | 441/80 |
| 3,449,776 | A * | 6/1969 | Brock | 5/627 |
| 5,179,746 | A * | 1/1993 | Rogers | 5/625 |
| 5,334,133 | A * | 8/1994 | Carroll | 602/18 |
| 6,081,947 | A * | 7/2000 | Disher | 5/632 |
| 7,082,632 | B2 * | 8/2006 | Hood | 5/625 |

* cited by examiner

*Primary Examiner* — Michael Brown
(74) *Attorney, Agent, or Firm* — Tod R. Nissle, P.C.

(57) ABSTRACT

A support assembly for an individual lying in a supine position comprises a first support unit, a second support unit, a first bridge slidably detachably engaging the first and second support units, a head rest, a second bridge detachably interconnecting the head rest and the first support unit, and a hinged torso compression alert strap mounted on and extending over the first support unit and including an indicator reflecting the degree of compression achieved by tightening the strap against the chest of an individual lying supine on the support assembly.

1 Claim, 10 Drawing Sheets

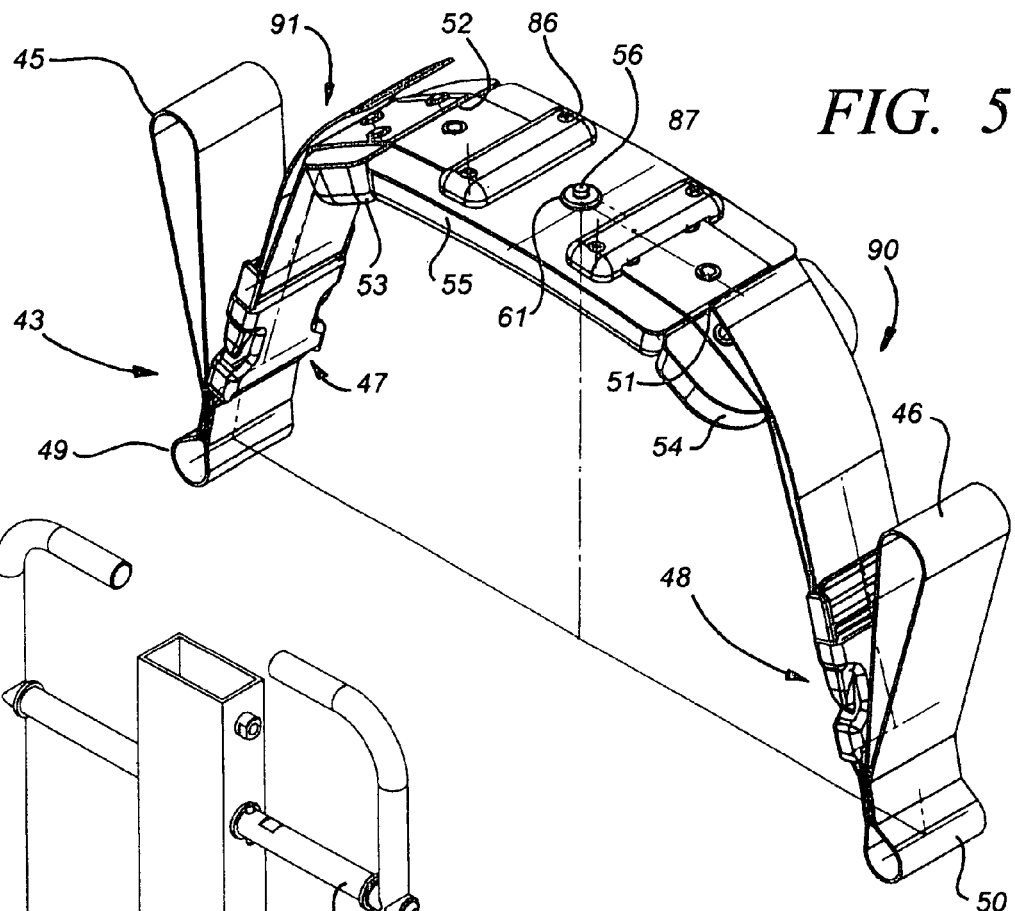

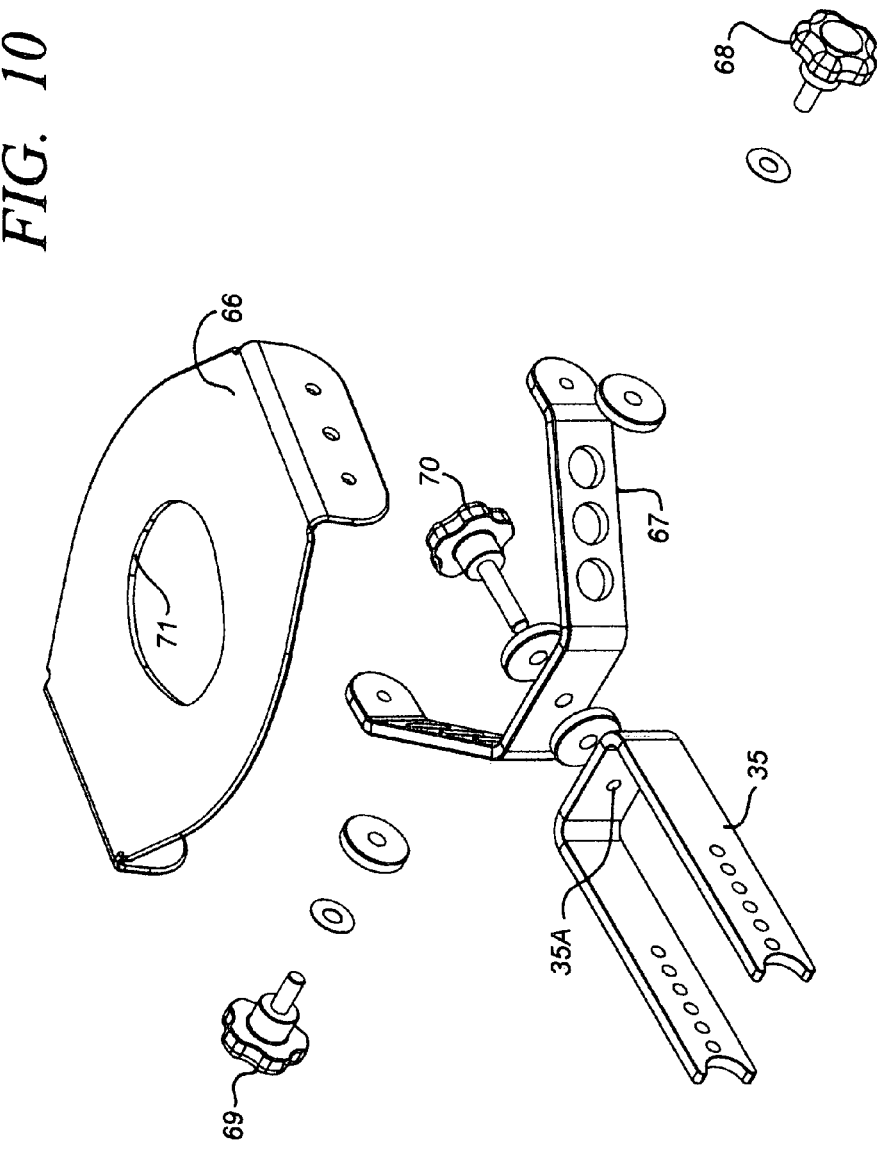

MODULAR SUPPORT SYSTEM

This application claims priority based on provisional patent application Ser. No. 61/686,866, filed Apr. 13, 2012.

This application pertains to a method and apparatus for supporting at least a portion of an individual's body.

In a further respect, the application pertains to a method and apparatus to support an individual lying prone or supine.

Those of skill in the art have, for many years, endeavored to provide improved apparatus and methodology for support portion's of an individual's body. Therefore, it would be highly desirable to provide an improved apparatus and method in this respect.

Therefore, it is a principal object of the instant invention to provide an improved apparatus and method to provide support for at least a portion of an individual's body.

A further object of the invention is to provide an apparatus and process to secure and stabilize in fixed position at least a portion of an individual's body.

These, and other and further objects of the invention will be apparent to those skilled in the art from the following detailed description thereof, taken in conjunction with the drawings, in which:

FIG. 5 is a perspective view illustrating the torso compression alert strap utilized in the apparatus of FIGS. 1 and 2;

FIG. 6 is a perspective view illustrating the skeletal support structure in the apparatus of FIG. 3;

FIG. 10 is an exploded perspective view illustrating further construction details of the headrest of FIG. 9;

Figure 1:
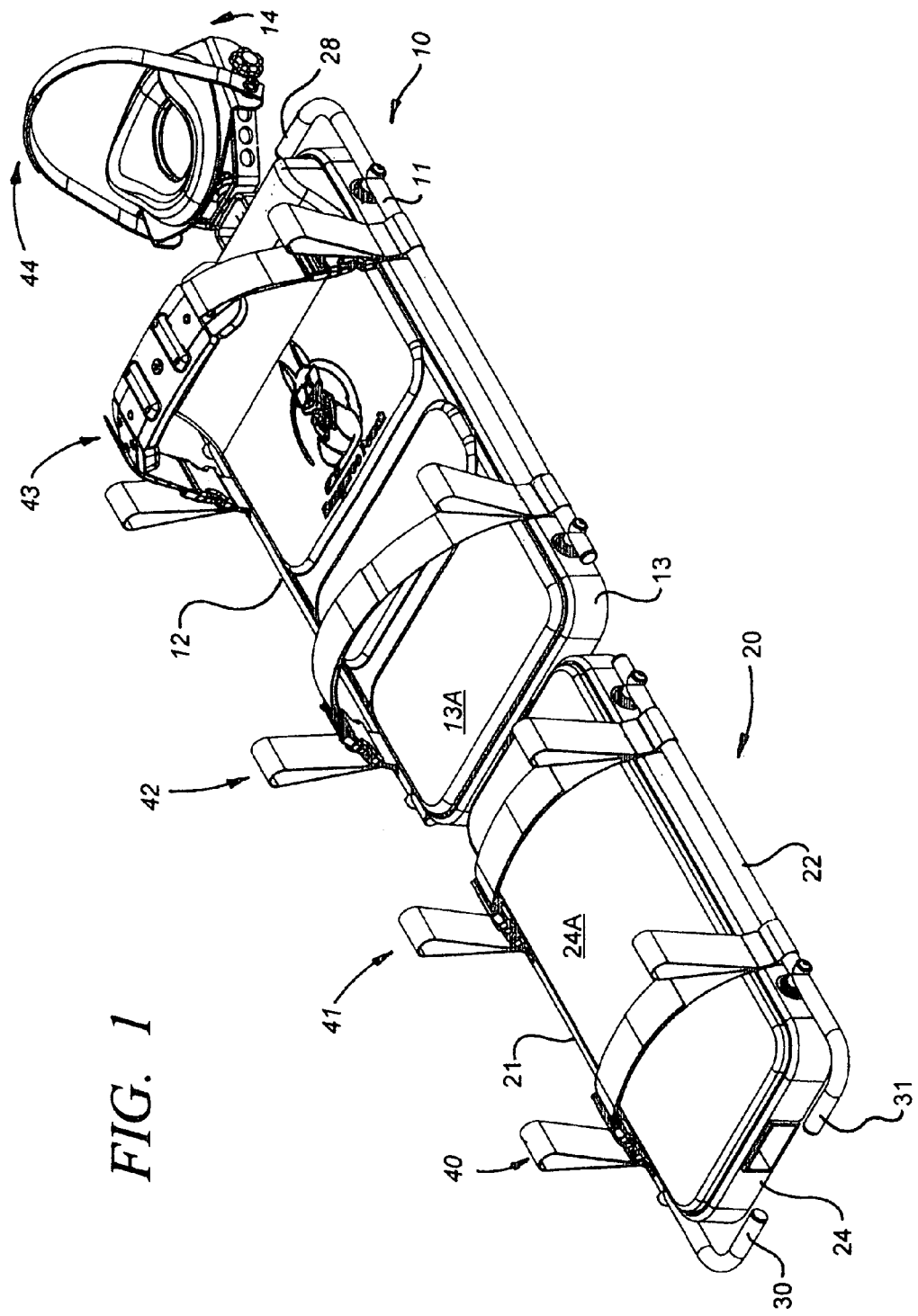
FIG. 1 is a perspective view illustrating modular support apparatus constructed in accordance with the principles of the invention.
Figure 2:
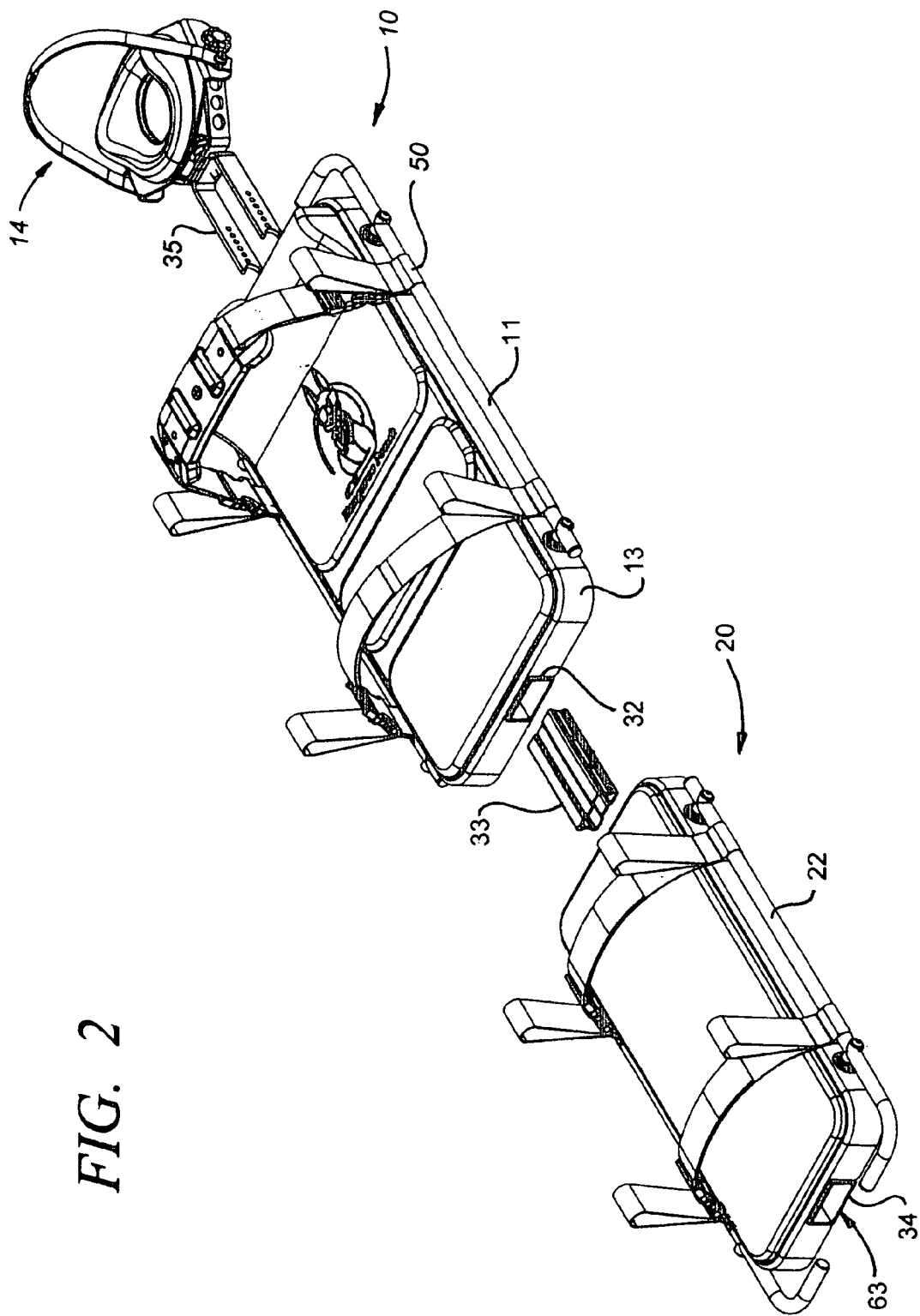
FIG. 2 is an exploded perspective view illustrating the partial sliding disassembly of the apparatus of FIG. 1.

Briefly, in accordance with the invention, provided is an improved support assembly for an individual lying in a supine position on the support assembly. The support assembly comprises a first support unit having a first length and including a first hollow spine with first and second open ends; a second support unit having a second length and including a second hollow spine with primary and secondary open ends, the second length being less than the first length; and, a first bridge slidably engaging the second end of the first spine and the primary end of the second spine to detachably interconnect the first and second support units such that the second unit can be detached from the first unit and used separately from the first unit. The support assembly also includes a head rest; and, a second bridge interconnecting the head rest and the first end of the first support unit. The second bridge is shaped and dimensioned to interconnect the head rest and one of the primary end and the secondary end of the second support unit. The support assembly also includes a hinged torso compression alert strap mounted on and extending over the first support unit and including an indicator reflecting the degree of compression achieved by tightening the strap against the chest of an individual lying supine on the support assembly.

Turning now to the drawings, which depict the presently preferred embodiments of the invention by way of illustration, and not limitation, of the invention, and in which like reference characters refer to corresponding elements throughout the several views, FIGS. 1 to 12 illustrate a modular support system constructed in accordance with the principles of the invention.

FIG. 1 illustrates an embodiment of the invention in which the support assembly is fully assembled and includes a first unit 10, a second unit 20, and a head rest 14. Unit 10 includes generally orthogonal panel 13. Handles 11 and 12 are each attached along and spaced apart from a different one of the right hand and left hand sides of board 13, respectively. Handle 11 includes turned in end 23. Handle 12 includes turned in end 24 (FIG. 8) spaced apart from and opposed to end 23. In a similar manner, handles 21 and 22 are each attached along and spaced apart from a different one of the left hand and right hand sides of board 24, respectively, of unit 20. Handle 22 includes turned in end 31. Handle 21 includes turned in end 30. Padding 13A, 24A can, if desired, be mounted on boards 13, 24, respectively, in the manner illustrated in FIGS. 1 and 2.

The support assembly of FIG. 1 includes strap assemblies 40, 41, 42, and 43. Strap assembly 43 comprises a hinged torso compression alert strap which is described below in more detail. The ends of each strap assembly 40 to 43 include a smaller loop sized to slide onto an appropriate handle 11, 12, 21, 22 in the manner illustrated in FIGS. 1 and 2. The ends of each strap assembly also each include a larger upstanding loop (for example, loops 45 and 46 in FIG. 5) which can be utilized as a handle to lift or otherwise position the support assembly. If desired, the ends of each strap assembly 40 to 42 can be configured to facilitate quick removal of the strap assembly from a handle 11, 12, 21, 22. For example, each end of a strap assembly 40 to 42 can include a quick release buckle unit comparable to buckle units 47 and 48 in FIG. 5. Incorporating each end of a strap assembly 40 to 42 a quick release buckle unit 47, 48 would also facilitate being able to detach assembly 43, detach a strap assembly 40 to 42, and substitute assembly 43 for the detached strap assembly 40 to 42.

Figure 4:
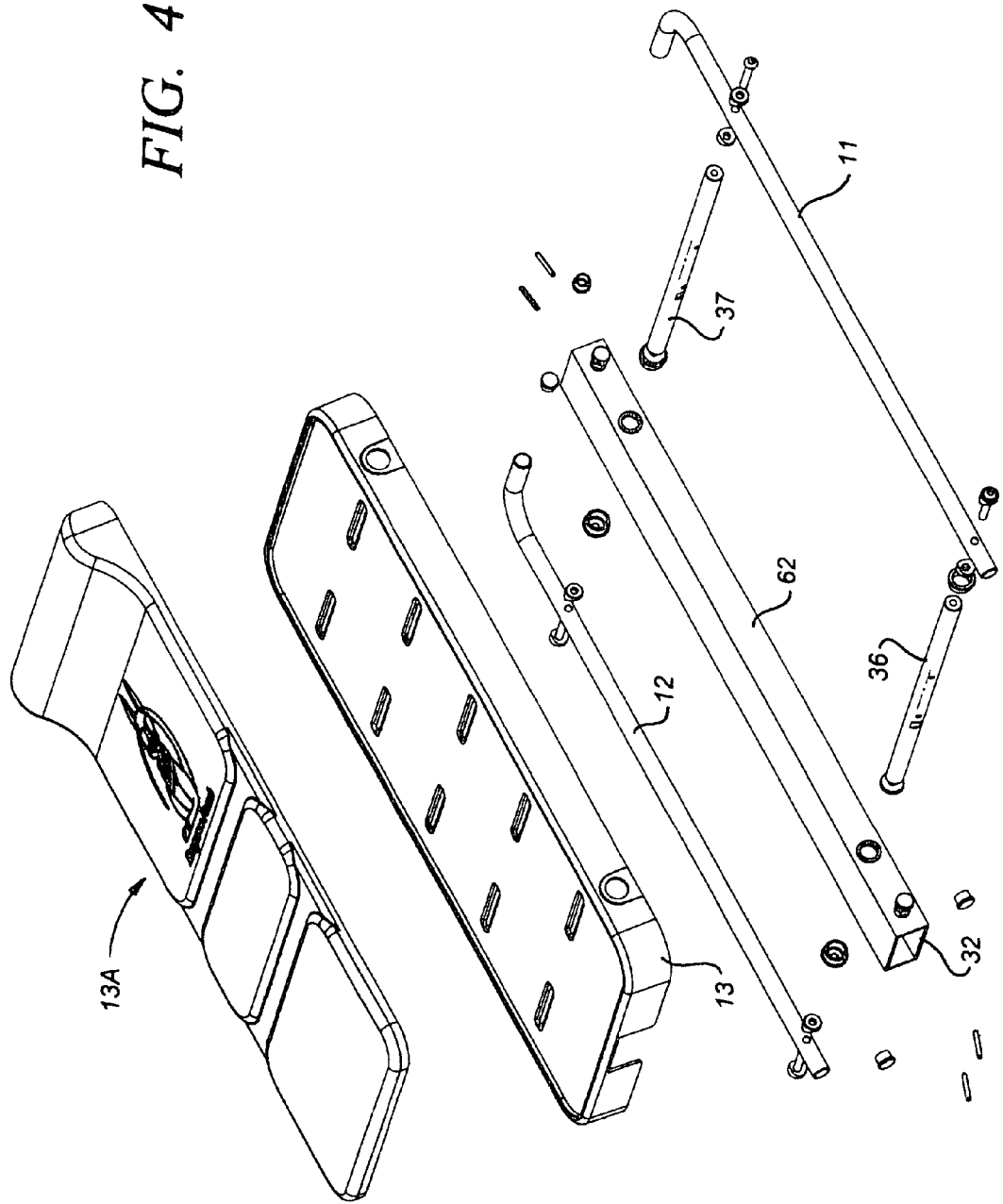
FIG. 4 is an exploded perspective view further illustrating the apparatus of FIG. 3.
Figure 8:
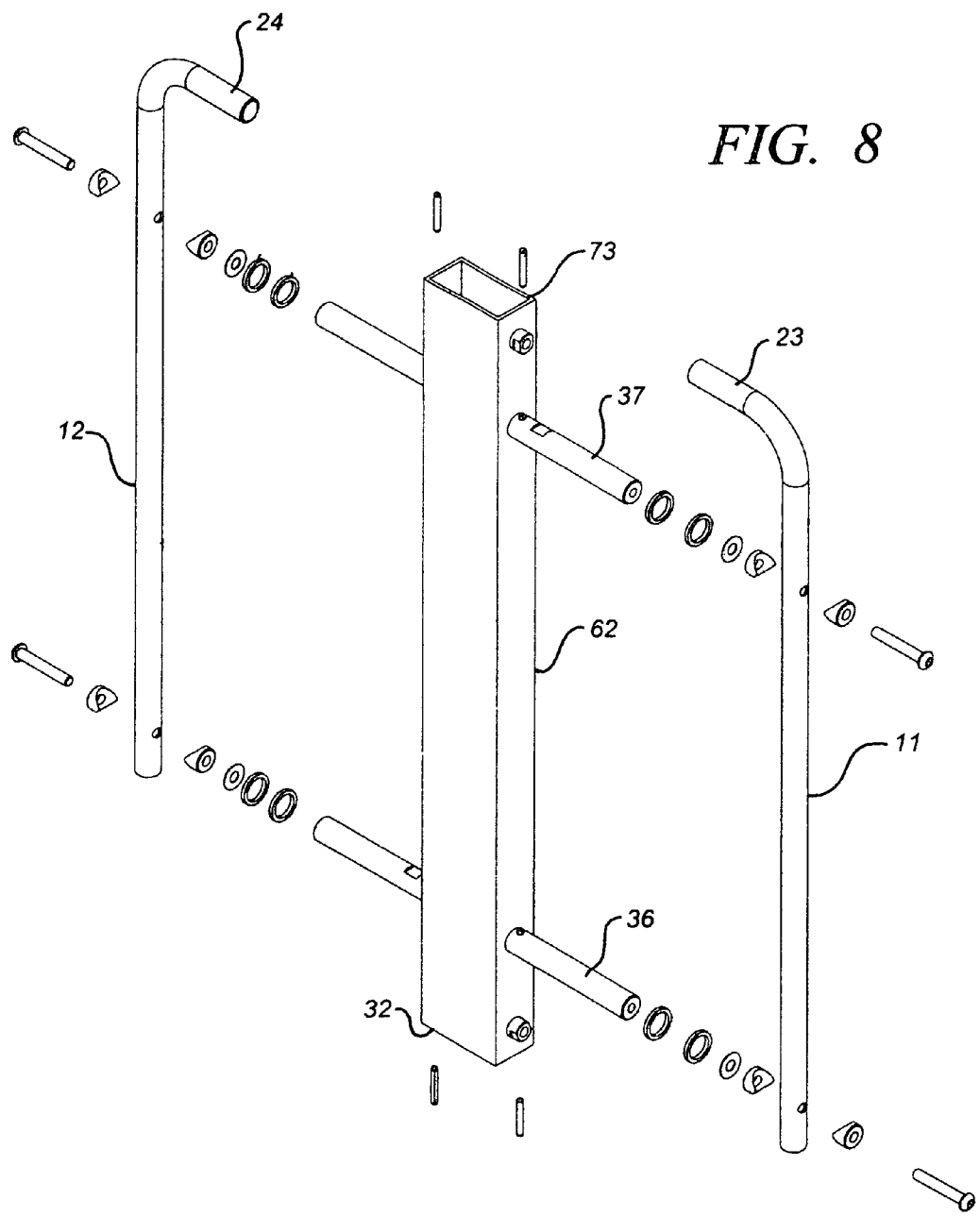
FIG. 8 is an exploded perspective view further illustrating the skeletal support structure of FIG. 6.

Hollow orthogonal spine 62 is mounted on the underside of board 13 (FIG. 4). Spine 62 includes open ends 32 (FIG. 4) and 73 (FIG. 8). Second unit 20 includes a hollow orthogonal spine 63 (FIG. 2) that, in a manner similar to that of spine 62 in unit 10, extends the length of unit 20. Spine 63, like spine 62, includes a pair of open ends. Open end 34 of spine 63 is visible in FIG. 2 at the bottom of unit 20. The other open end, the "upper" open end, is at the top of unit 20 in FIG. 2 but is not visible.

Figure 3:
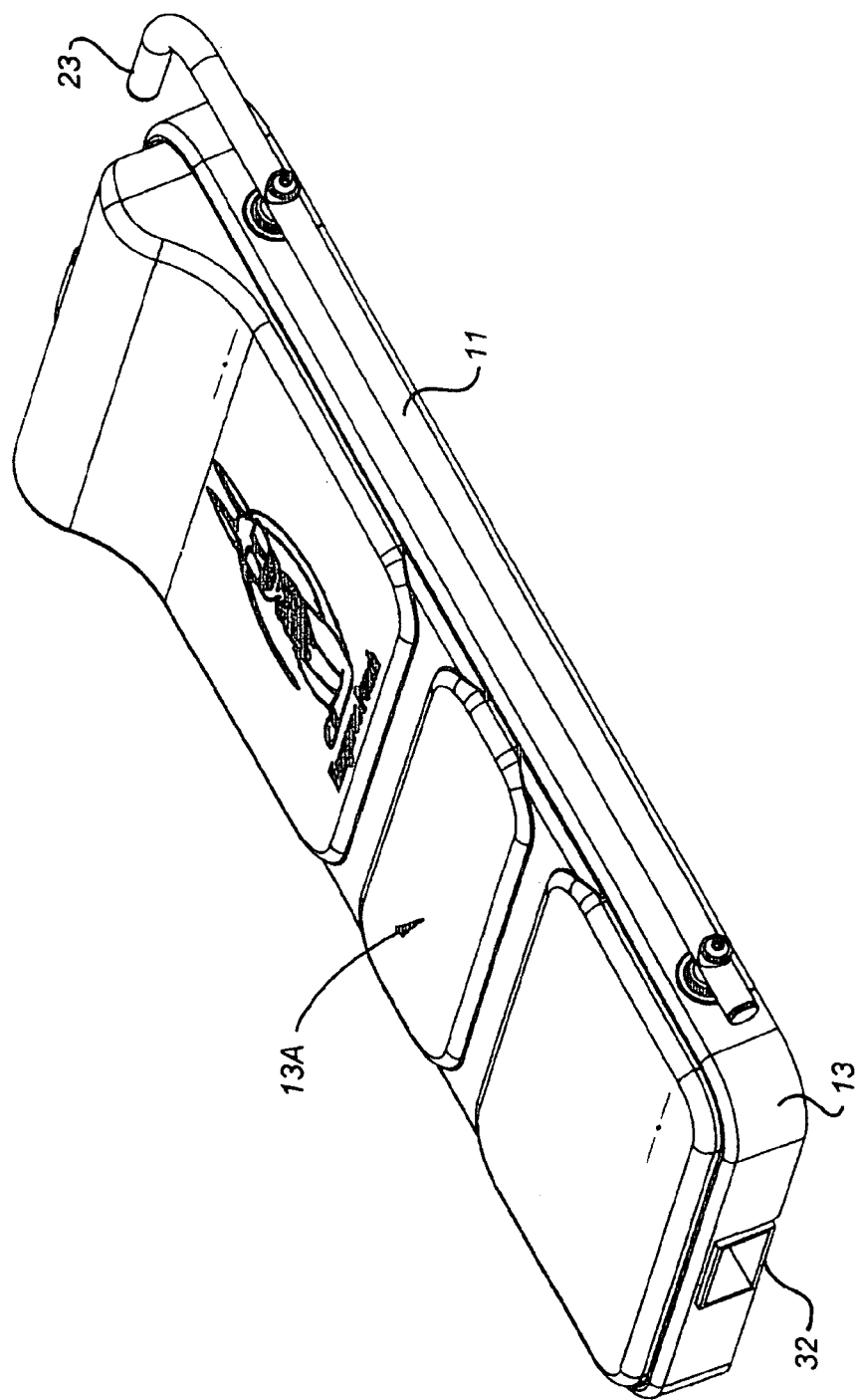
FIG. 3 is a perspective view illustrating construction details of a portion of the apparatus of FIG. 1.

The first unit 10 is illustrated in FIG. 3 without its operatively associated strap assemblies 42 and 43. FIG. 4 is an exploded perspective view of unit 10 of FIG. 3. Spine 62 is readily viewed in FIG. 4, as are cross members 36, 37 which interconnect handles 11 and 12. FIG. 8 is an exploded perspective view of spine 62, members 36 and 37, and handles 11 and 12. FIG. 6 illustrates spine 62, members 36 and 37, and handles 11 and 12 assembled.

Figure 7:
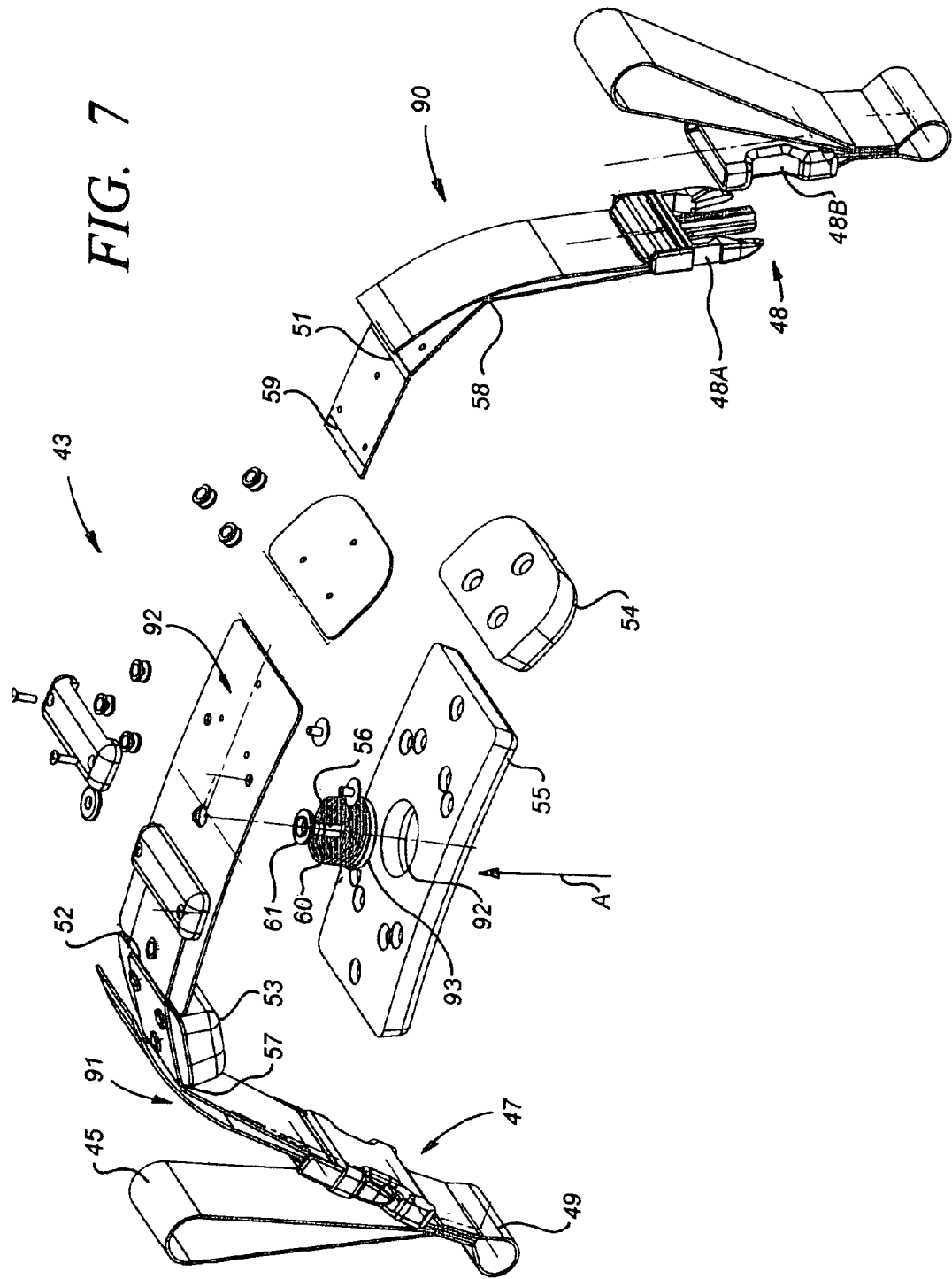
FIG. 7 is an exploded perspective view illustrating further construction details of the torso compression alert strap of FIG. 5.

The strap assembly 43 is illustrated in more detail in FIGS. 5 and 7. Assembly 43 includes smaller loops 49 and 50 sized to be slidably mounted on handles 12 and 11, respectively, in the manner illustrated in FIGS. 1 and 2. Assembly 43 also includes larger upstanding loops 45 and 46 which are utilized as handles to lift or otherwise position the support assembly. Buckle units 47 and 48 are identical and each include a polymer spring clip 48A which is removably received by and latches in a hollow sleeve 48B. As would be appreciated by those of skill in the art, insertion and removal of clip 48A in sleeve 48B is accomplished manually.

Of particular importance is the hinged construction of the portions of the strap assembly which extends intermediate buckle units 47 and 48. Strap portions 90 and 91 are identical. Strap portion 90 extends from anchor 87 to buckle unit 48. Strap portion 91 extends from anchor 86 to buckle unit 47. Strap portions 90, 91 are each fabricated from a pliable and/or bendable material. By way of example, and not limitation, portions 90, 91 can be fabricated from ballistic nylon, from another woven material, or from leather.

Section or strip 51 of portion 90 extends laterally across portion 90 and, in operation, bends and functions as a hinge. Section 58 of portion 90 also extends laterally across portion 90 and, in operation, bends and functions as a hinge. Portion 90 can comprise, for example, a continuous length or strip or strap of a pliable or woven material.

Section 52 of portion 91 extends laterally across portion 91 and, in operation, bends and functions as a hinge. Section 57 of portion 91 also extends laterally across portion 91 and, in operation, bends and functions as a hinge. Portion 90 can comprise, for example, a continuous length or strip or strap of a pliable, bendable woven material.

Compressible foam pad 54 is attached to and mounted on the underside of portion 90. Compressible foam pad 53 is attached to and mounted on the underside of portion 91. Compressible foam pad 55 is attached to and mounted on the underside of panel member 92. Member 92 preferably, but not necessarily, is pliable such that it can bend and contour to the torso (or back) of an individual lying supine (or prone) on the support assembly of FIG. 1. One end of portion 90 is secured to panel member 92 by anchor 87. The other end of portion 90 is secured to buckle unit 48. One end of portion 91 is secured to panel member 92 by anchor 86. The other end of portion 91 is secured to buckle unit 47.

Cylindrical spring 60 rests on and upwardly depends from thin circular panel member 93. The lower end (not visible) of upwardly extending cylindrical indicator 56 is fixedly secured to the center of member 93. Indicator 56 is presently relatively small and comprises an upstanding cylindrical pin or tube. Indicator 56 extends upwardly through the central open area circumscribed by spring 60. Panel member 93, and therefore spring 60 and indicator 56, seats in cylindrical opening 92 formed in foam pad 55. The distal end of indicator 56 can be colored to facilitate the visual identification of indicator 56 during operation of the strap assembly.

In operation of the strap assembly 43, when assembly 43 is tightened against the torso (or back) of an individual lying supine (or prone) on the support assembly of FIG. 1, pressure is generated by the torso of the individual pressing against pad 55 in the direction of arrow A. When the pressure increases a sufficient amount, pad 55 compresses and, as a consequence, spring 60 compresses. Compressing spring 60 displaces indicator 56 upwardly in the direction of arrow A and displaces the distal end of indicator 56 upwardly through an opening in the center of fixed rivet 61. When the distal end of indicator 56 is displaced a sufficient distance upwardly through the opening in rivet 61, the distal end is visible and the medical personnel tightening strap assembly 43 know that the assembly has been sufficiently tightened. If desired, the distal end of indicator 56 can include a plurality of colors. For example, the tip of the distal end may be green. The next section, below the green, may be yellow. The next section, below the yellow, may be red. If only the green tip of indicator 56 becomes visible when strap assembly 43 is tightened, medical personnel know the strap has been tightened sufficiently and likely will not injure an individual lying supine (or prone) on the support assembly. If the strap assembly 43 is tightened further and the distal end of indicator 56 protrudes a sufficient distance above rivet 61 for both the green and yellow portions of indicator 56 to be visible, that suggests that caution should be utilized, that the strap assembly 43 should not be tightened further, and that the strap assembly 43 preferably is loosened so that only the green tip of indicator 56 is visible. If after strap assembly 43 is tightened, the green, yellow, and red portions of the distal end of indicator 56 extend above rivet 51 and are visible, that suggests that the strap assembly 43 should be loosened until only the green, or the green and yellow, portion of the distal end of indicator 56 is visible.

Spring 60 and indicator 56 function as part of a sensor unit which indicates or measures the force generated by strap assembly 43 against the torso (or back) of an individual lying on the support assembly of FIG. 1. As would be appreciated by those of skill in the art, electronic sensor units or other sensor units can be utilized on strap 43 in place of or in combination with the sensor unit which utilizes spring 60 and indicator 56. For example, a pressure sensor can be incorporated in strap assembly which includes an alphanumeric digital readout which indicates the pressure generated by strap assembly 43 against the torso of an individual lying on the support assembly of FIG. 1.

In FIG. 1, headrest 14 is removably secured to unit 10. Headrest 14 includes a U-shaped neck 35 which is slidably received by opening 73 (FIG. 8) in the upper end of spine 62 (FIGS. 4, 6, 8). Headrest 14 can, if desired, be slidably removed from opening 73 and neck 35 can be inserted in the opening 34 (FIG. 2) formed in the lower end of spine 63 of unit 20. Neck 35 can also be slidably inserted in opening 32 at the bottom of spine 62, and can be slidably inserted in the opening formed in the upper end (not visible) of spine 63.

Units 10 and 20 are detachably interconnected by removably, slidably inserting one end of bridge member 33 (FIG. 2) in the opening 32 in the lower end of spine 62 and the other end of member 33 in the opening (not visible) formed in the upper end of spine 63. After member 33 is so inserted to interconnect units 10 and 20 in the configuration illustrated in FIG. 1, set screws or any other desired fastening apparatus can be utilized to secure detachably member 33 in spines 62, 63. Set screws or any other desired fastening apparatus can be utilized to secure detachable neck 35 in spine 62, 63.

Figure 12:
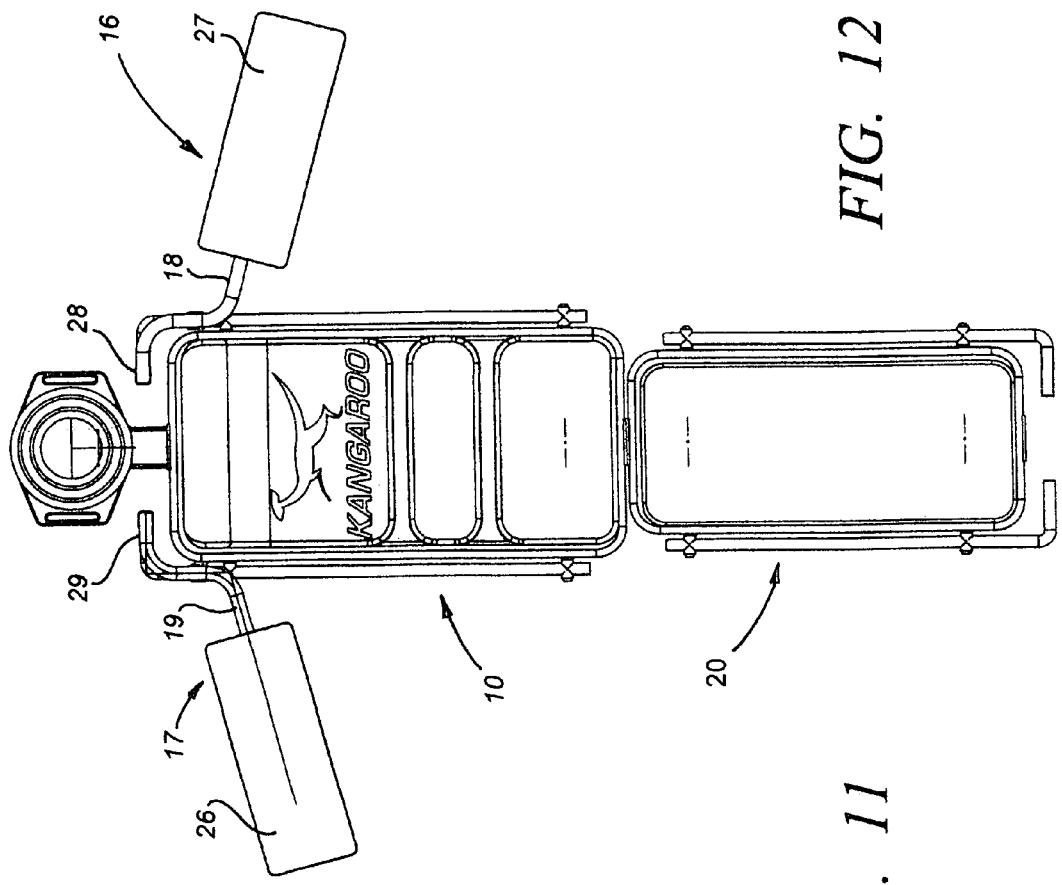
Figure 11:
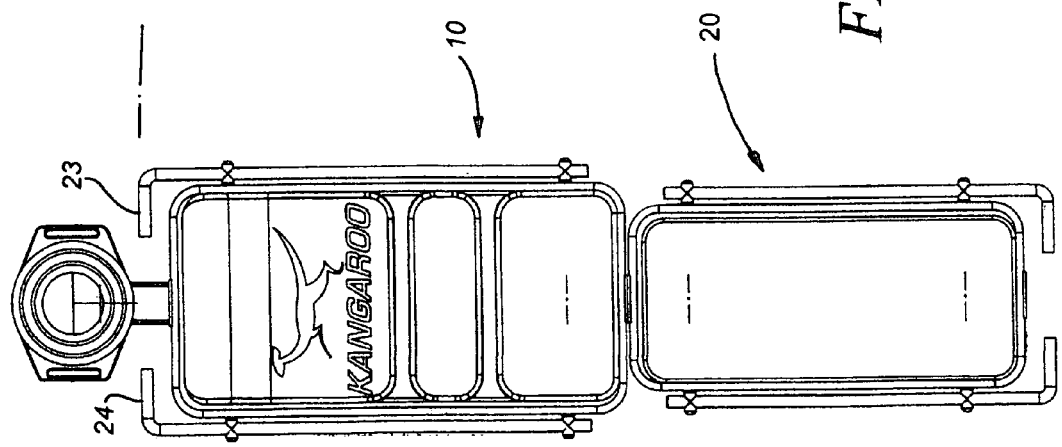
FIG. 11 is a top view of modular support apparatus constructed in accordance with the principles of the invention; and, FIG. 12 is a top view of the apparatus of FIG. 11 will removable adjustable armrests incorporated therein.

In FIG. 12, wing 16 includes tubular arm 18 connected to orthogonal arm rest or panel 27. Wing 17 includes tubular arm 19 connected to orthogonal arm rest or panel 26. A short length of a first hollow cylindrical tube (not visible) is welded or otherwise secured to the underside of the distal end 28 of arm 18. A short length of a second hollow cylindrical tube (not visible) equivalent in shape and dimension to the first hollow cylindrical tube is welded or otherwise secured to the underside of the distal end 29 of arm 19. The first hollow cylindrical tube is shaped and dimensioned to slide over end 23 of handle 11 so that wing 16 can be mounted on end 23 in the configuration illustrated in FIG. 12. The second hollow cylindrical tube is shaped and dimensioned to slide over end 24 of handle 12 so that wing 17 can be mounted on end 24 in the configuration illustrated in FIG. 12. Each arm 18, 19 can be constructed such that each arm 18, 19 can be extended, rotated, or otherwise adjusted to alter the orientation of panels 27 and 26, respectively, when they are mounted on unit 10 (or unit 20). As would be appreciated by those of skill in the art, in an alternate configuration of the invention, the first and second hollow cylindrical tubes can be shaped and dimensioned to also be removably slidably mounted on ends 30 and 31 of handles 21 and 22, respectively, so that wings 16 and 17 can be mounted on unit 20. Any desired construction can be utilized to mount a wing 16, 17 on the support assembly of FIG. 1.

Figure 9:
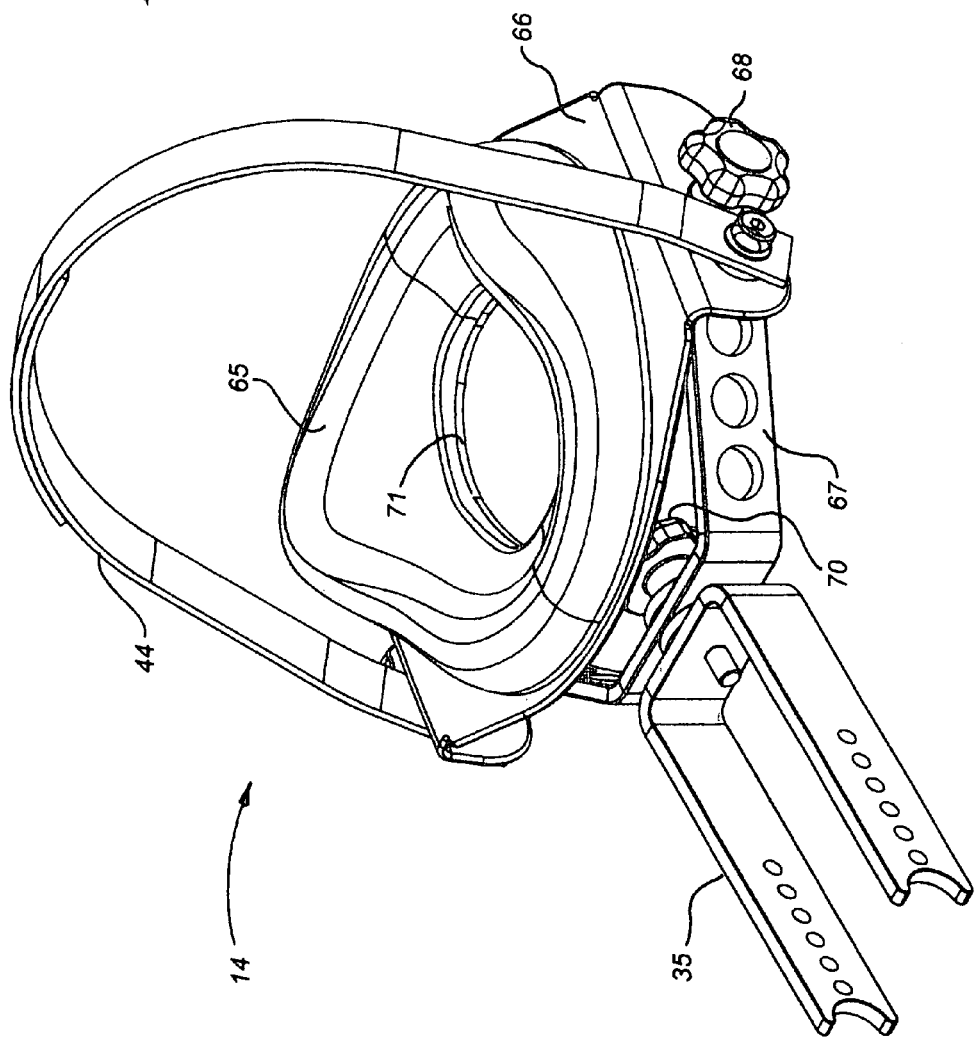
FIG. 9 is a perspective view illustrating the headrest utilized in the apparatus of FIGS. 1 and 2.

The construction of head rest 14 is illustrated in more detail in FIGS. 9 and 10. Central aperture 71 is formed through generally oval support plate 66. Contoured soft foam head support 65 is mounted on plate 66. V-shaped bracket 67 is secured to downwardly depending flanges on plate 66 with fasteners 68 and 69. Fastener 70 secures bracket 67 to U-shaped neck 35. The ends of strap 44 each are attached to a different one of the flanges which downwardly depend from the sides of plate 66. Neck 35 and opening 73 (FIG. 8) are shaped and dimensioned such that head rest 14 can, in FIG. 1, be slidably removed from spine 62 of unit 10, rotated 180 degrees about the longitudinal axis of unit 10, and slidably re-inserted in aperture 73 and spine 62. In an alternate embodiment of the invention, the location of aperture 35A in neck 35 can be moved from the centralized location illustrated in FIG. 10 up or down or laterally to facilitate rotating bracket 67 about the longitudinal axis of fastener 70 in order, for example, to rotate plate 66 and support 65 simultaneously with bracket 67 through an arc of one hundred and eighty degrees (or another arc having a length other than 180 degrees) to invert or otherwise alter the orientation of plate 66, bracket 67, and support 65. Consequently, for example, instead of forming aperture 35A through neck 35 at the location shown in FIG. 10, aperture 35A can be formed through neck 35 at a location above that shown in FIG. 10.

As can be seen in FIG. 1, the length of unit 10 is greater than the length of unit 20. And, the length of each handle 11, 12 is greater than the length of each handle 21, 22. Handles 11, 12 are parallel to the length of unit 10. Handles 21, 22 are parallel to the length of unit 20. One important feature of the invention is that unit 20 can be detached from unit 10 (or vice versa) by sliding unit 20 off bridge 33 and used separately, either for children or in circumstances where both units 10 and 20 are not required. A strap assembly comparable to strap assembly 43 can be utilized on unit 20. Head rest 14 can, as previously described, be mounted on unit 20 by inserting U-shaped neck through aperture 34 in slide 63.

Having described the invention in such terms as to enable those skilled in the art to make and use the invention, and having described presently preferred embodiments thereof,

We claim:

1. A support assembly for an individual lying in a supine position, said assembly comprising
   (a) a first support unit having a first length and including a first hollow spine with first and second open ends;
   (b) a second support unit having a second length and including a second hollow spine with primary and secondary open ends, said second length being less than said first length;
   (c) a first bridge slidably engaging said second end of said first spine and said primary end of said second spine to detachably interconnect said first and second support units such that said second unit can be detached from said first unit and used separately from said first unit;
   (d) a head rest;
   (e) a second bridge interconnecting said head rest and said first end of said first support unit, said second bridge being shaped and dimensioned to interconnect said head rest and one of said primary end and said secondary end of said second support unit;
   (f) a hinged torso compression alert strap mounted on and extending over said first support unit and including an indicator reflecting the degree of compression achieved by tightening the strap against the chest of an individual lying supine on the support assembly.

\* \* \* \* \*